(12) United States Patent
Bowles

(10) Patent No.: US 10,408,615 B2
(45) Date of Patent: Sep. 10, 2019

(54) METHOD OF INSPECTING A DEGRADED AREA OF A METAL STRUCTURE COVERED BY A COMPOSITE REPAIR AND METHOD OF MEASURING A REMAINING WALL THICKNESS OF A COMPOSITE STRUCTURE

(71) Applicant: INVERSA SYSTEMS LTD., Fredericton (CA)

(72) Inventor: John T. Bowles, Islandview (CA)

(73) Assignee: INVERSA SYSTEMS LTD., Fredericton (CA)

( * ) Notice: Subject to any disclaimer, the term of this patent is extended or adjusted under 35 U.S.C. 154(b) by 292 days.

(21) Appl. No.: 15/518,717

(22) PCT Filed: Oct. 14, 2015

(86) PCT No.: PCT/CA2015/051033
§ 371 (c)(1),
(2) Date: Apr. 12, 2017

(87) PCT Pub. No.: WO2016/058095
PCT Pub. Date: Apr. 21, 2016

(65) Prior Publication Data
US 2017/0248417 A1 Aug. 31, 2017

Related U.S. Application Data

(60) Provisional application No. 62/063,785, filed on Oct. 14, 2014.

(51) Int. Cl.
*G01B 15/02* (2006.01)
*G01N 23/20* (2018.01)
*G01N 23/20066* (2018.01)

(52) U.S. Cl.
CPC ....... *G01B 15/02* (2013.01); *G01N 23/20066* (2013.01); *G01N 2223/063* (2013.01);
(Continued)

(58) Field of Classification Search
CPC ............ G01B 15/02; G01N 23/20066; G01N 2223/063; G01N 2223/628; G01N 2223/633; G01N 2223/646
See application file for complete search history.

(56) References Cited

U.S. PATENT DOCUMENTS 5,195,117 A * 3/1993 Ong .................. G01B 15/02
378/70
5,665,913 A 9/1997 Chung
(Continued)

FOREIGN PATENT DOCUMENTS

CA 2248145 A1 9/1997
WO 2014124522 A1 8/2014

*Primary Examiner* — Don K Wong
(74) *Attorney, Agent, or Firm* — Norton Rose Fulbright Canada LLP; Alexandre Daoust

(57) ABSTRACT

The method of inspecting a degraded area of a metal structure covered by a composite repair generally comprises operating a Compton scattering inspection device onto the degraded area, including emitting a beam of radiation particles directed towards and across the composite repair, detecting at least some backscattered photons scattered back from the metal structure, and acquiring Compton scattering data from the detected backscattered photons, the Compton scattering data being indicative of remaining wall thickness of the degraded area.

7 Claims, 4 Drawing Sheets

(52) U.S. Cl.
CPC . *G01N 2223/628* (2013.01); *G01N 2223/633* (2013.01); *G01N 2223/646* (2013.01)

(56) References Cited

U.S. PATENT DOCUMENTS 5,896,429 A 4/1999 Lanza et al.
2002/0194916 A1 12/2002 Yamada et al.

\* cited by examiner

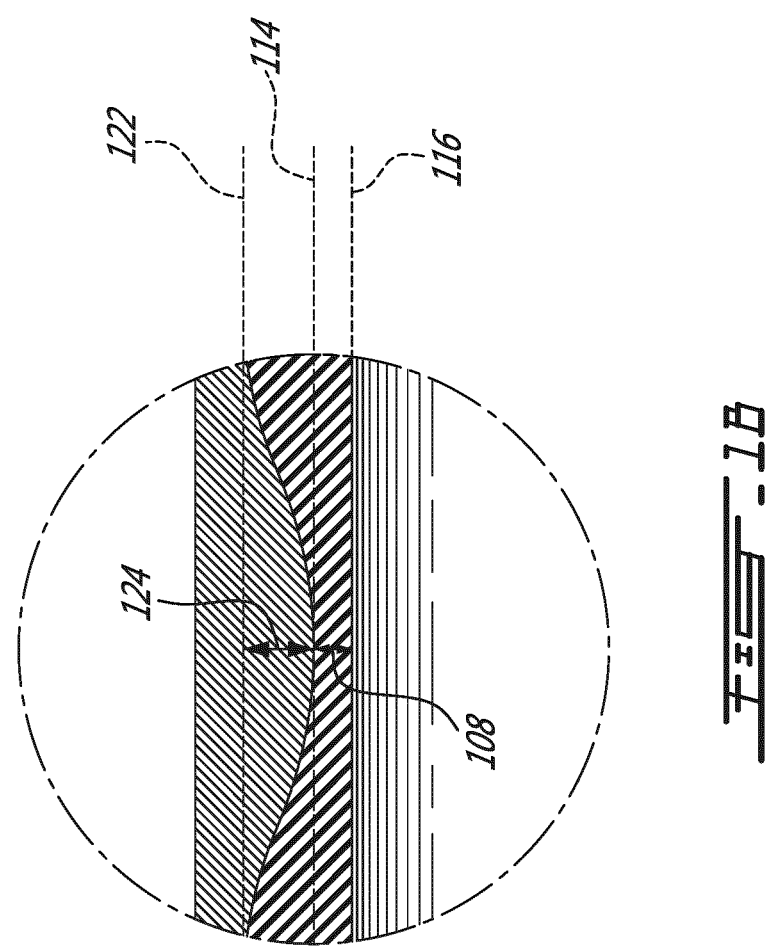

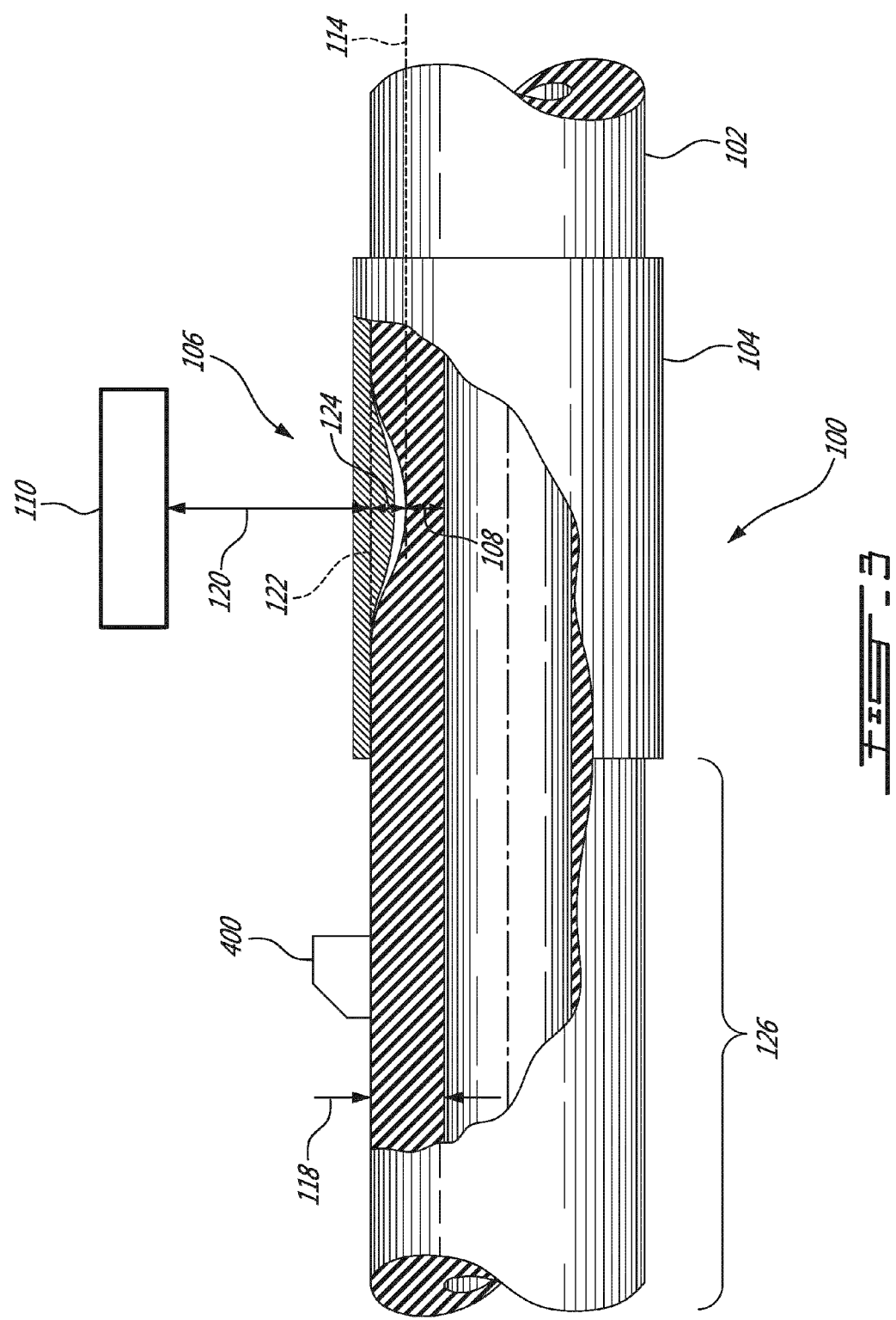

METHOD OF INSPECTING A DEGRADED AREA OF A METAL STRUCTURE COVERED BY A COMPOSITE REPAIR AND METHOD OF MEASURING A REMAINING WALL THICKNESS OF A COMPOSITE STRUCTURE

CROSS-REFERENCE TO RELATED APPLICATION

This patent application claims priority of U.S. provisional Application Ser. No. 62/063,785, filed on Oct. 14, 2014, the contents of which are hereby incorporated by reference.

FIELD

This specification relates generally to technologies and methods for the condition assessment of composite repairs on pressured piping and pressure vessels.

BACKGROUND

Industrial assets such as pressurized piping and pressure vessels used in the oil and gas sector are commonly subject to corrosion and other degradation. Degradation can become severe enough to compromise the integrity of the asset. In the case of pressure piping and pressure vessels, it is common practice to apply composite wrap repairs to affected areas to avoid shutdowns associated with replacement or removal of the asset. The composite wrap repair is applied to the external surface of the pipe or vessel and can temporarily provide satisfactory integrity of the asset until a permanent solution can be applied.

A typical composite wrap includes fibres reinforced with an epoxy resin. The fibre reinforcements are either carbon or glass. Various epoxy resins are selected based on the overall design conditions and installation temperature of a repair. The wrap repair reinforces the damaged area and also prevents further degradation and/or corrosion.

Once the composite wrap is applied, it can hinder or impede subsequent inspection of the pipe or vessel, and thus quantification of further degradation beneath the composite wrap. Moreover the integrity of the repair itself can be difficult to assess.

There thus always remains room for improvement.

SUMMARY

There was a need for a means to inspect the integrity of the wrap repair and a need for a means to monitor degradation beneath the wrap repair as being able to know such states with greater accuracy could allow making more informed decisions and potentially allow to prolong the use of the wrap repair rather than moving to a permanent solution based on the fear that a status is worse than it is. Significant benefits could be gained from prolonging the term of use for the composite wrap repairs (fewer shutdowns, etc).

In accordance with one aspect, there is provided a method of inspecting a degraded area of a metal structure covered by a composite repair, the method comprising: operating a Compton scattering inspection device onto the degraded area, including emitting a beam of radiation particles directed towards and across the composite repair, detecting at least some backscattered photons scattered back from the metal structure, and acquiring Compton scattering data from the detected backscattered photons, the Compton scattering data being indicative of remaining wall thickness of the degraded area.

In accordance with another aspect, there is provided a method of measuring a remaining wall thickness of a composite structure, the method comprising: performing an inspection of the composite structure having a plurality of portions; identifying one of the portions having an area of severe degradation based on the results of the inspection performed; operating a Compton scattering inspection device onto the area of severe degradation, in a manner to acquire at least an actual outer wall position data; using a computer, measuring the remaining wall thickness of the area of severe degradation using at least the outer wall position data; and generating a signal indicative of said remaining wall thickness.

In accordance with another aspect, there is provided a method of obtaining an indication of the integrity of a metal structure having an outer surface portion covered by a composite repair, the method comprising: determining an area of severe degradation on the outer surface portion of the metal structure; and measuring the pit depth of the surface portion at the area of severe degradation using a Compton scattering inspection device.

In accordance with another aspect, there is provided a method of obtaining an indication of the integrity of a metal structure having a surface portion covered by a non-metallic material, the method comprising: determining an area of severe degradation on the surface portion of the metal structure; and obtaining an indication of the integrity of the metal structure at the area of severe degradation using a Compton scattering inspection device.

In accordance with another aspect, there is provided a method of inspecting a plurality of composite repairs each adhered to a corresponding metal structure, the method comprising: visually inspecting the plurality of composite repairs; prioritizing the plurality of composite repairs based on the results of the visual inspection; and performing a more thorough, and at least partially automated inspection on a given one of the composite repairs based on the result of said prioritizing.

In this specification, the expression composite repair refers to a repair made of a fiber-reinforced material adhered against the substrate. Typically, the repair will include more than one layer of fibres such as glass, carbon, basalt or aramid set in a polymer matrix of epoxy, vinylester or polyester thermosetting plastic.

Many further features and combinations thereof concerning the present improvements will appear to those skilled in the art following a reading of the instant disclosure.

DESCRIPTION OF THE FIGURES

In the figures,

FIG. 1B is an enlarged cross-sectional view of an area of severe degradation of the metal pipe shown in FIG. 1A;

FIG. 3 is a schematic view of an example of a Compton scattering inspection device in a position to measure a remaining wall thickness of an area of severe degradation of the metal pipe, in accordance with another embodiment.

DETAILED DESCRIPTION

The failure mechanisms of composite repairs include ingress of water/oxygen under the wrap causing further corrosion/degradation of the asset, dis-bonding of the wrap from the asset which can reduce the ability of the asset to retain pressure and/or enable water/oxygen ingress. Continued corrosion/degradation of the asset can exist in combination with, or in the absence of the problems mentioned above.

The following information can be of relevance in determining whether or not a composite repaired asset or composite structure (e.g. pipe or vessel section having composite repair thereon) is fit for service: confirmation that the degradation of the asset under the wrapped area remains within acceptable limits; evidence that wrap is bonded to the asset, and evidence that layers of wrap are bonded to each other Conventional nondestructive testing (NDT) methods each have limits which can make them unsuitable to obtain such information. For instance, ultrasonic testing, typically used to determine wall thicknesses, is limited by the poor ultrasonic transmission properties of composite wrap material. Radiography (e.g. Profile and Double Wall Single Image digital radiography) can be useful on small diameter piping, but otherwise has very limited accuracy in providing information about shape and approximate depths of defects under the repaired area. Magnetic Particle, liquid penetrant testing and eddy current testing solutions are all ineffective to quantify wall loss under the composite material.

A Compton scattering inspection device technology has recently been developed, as presented in international patent publication WO 2014/124,522, the specification of which is hereby incorporated by reference. Compton scattering inspection devices, including the example referred to above, can be embodied as Computed Tomography devices in which case they can be referred to as Backscatter Computed Tomography (BCT) apparatus. Other types of Compton scattering inspection device may be used.

Figure 1A:
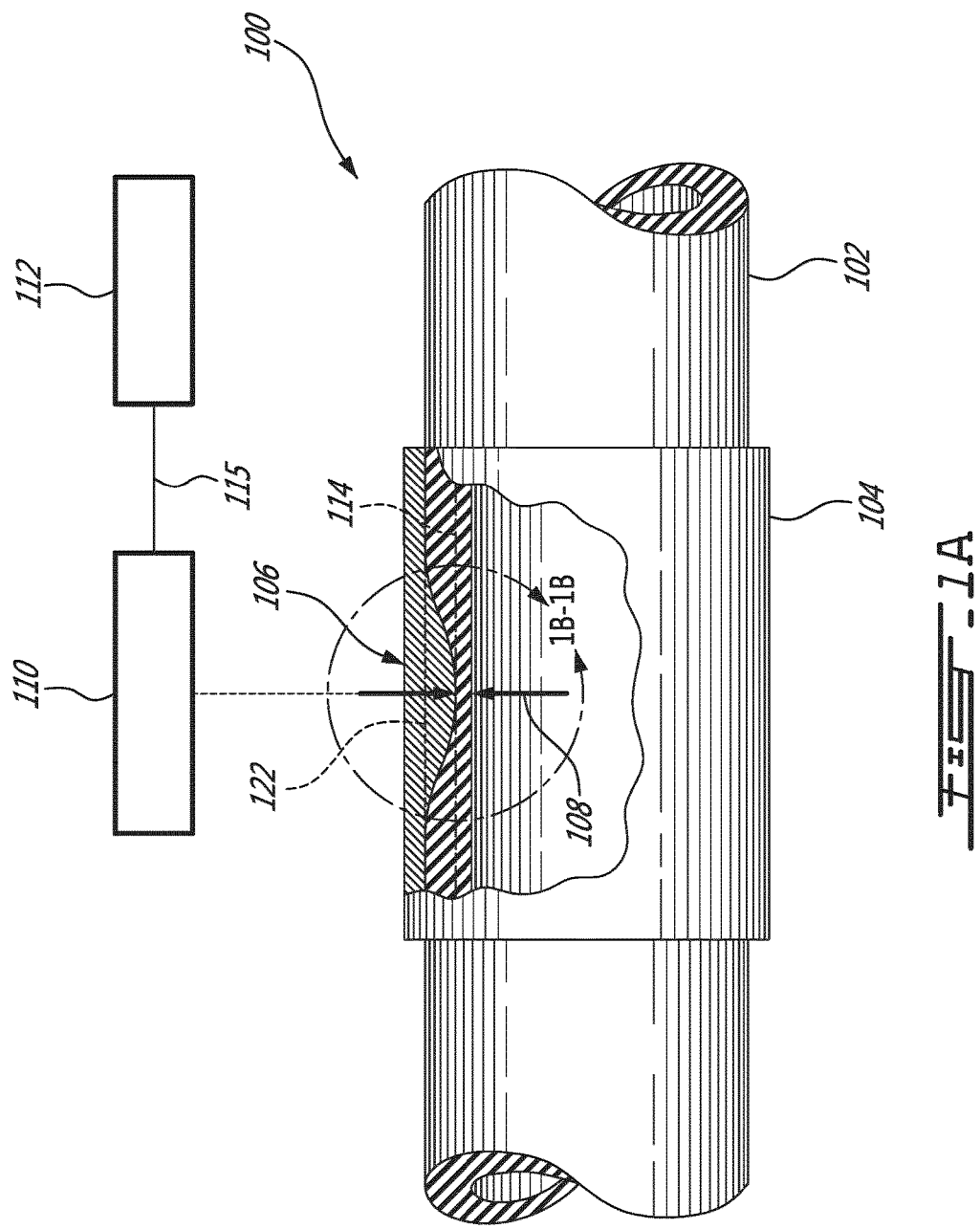
FIG. 1A is a schematic view of an example of a Compton scattering inspection device in position to measure a remaining wall thickness of a portion of a metal pipe shown in a partial and fragmented view, in accordance with an embodiment.

FIG. 1A shows an example of a composite structure 100, in accordance with an embodiment. The illustrated composite structure 100 is a metal pipe 102 covered by a composite wrap repair 104. The composite wrap repair 104 is shown to cover an area of severe degradation 106 of the metal pipe 102. As shown, the surface of the metal pipe 102 is damaged and has a wall having a reduced wall thickness. FIG. 1B shows an enlarged view of the area of severe degradation 106 and a remaining wall thickness 108. In the embodiment shown in FIGS. 1A-B, the area of severe degradation 106 has a defect which is embodied in the form of an expanding portion of the composite wrap repair 104 which compensates for the defect of the metal pipe 102 and which allows the defect to go relatively unnoticed from the outside. In another embodiment, such as the one shown in FIG. 3, the area of severe degradation 106 has a defect which creates a void space between the composite wrap repair 104 and the metal pipe 102. The area of severe degradation can include other types of defects.

Referring back to FIG. 1A, there is shown a Compton scattering inspection device 110 and a computer 112 configured to communicate data with one another. In this embodiment, during use, the Compton scattering inspection device 110 is configured to be received against the metal pipe 102 so that the Compton scattering inspection device 110 projects a beam of radiation particles (i.e. radiation that behaves as a particle), such as gamma-rays, x-rays and neutrons, towards and across the composite wrap repair 104 of the metal pipe 102. Backscattered photons, typically referred to as Compton scattering radiation, are then detected in order to generate the Compton scattering data. The number of backscattered photons detected is determined so as to obtain a statistically meaningful number of photons while maintaining a practical size, weight and speed for portable use with industrial facilities. The beam can be a pencil beam, a cone beam, and any suitable beam. In this embodiment, the computer 112 is shown to be connected to the Compton scattering inspection device 110 via a wireless or a wired connection 115. The computer 112 typically has a processor, a memory, a communication port and other components deemed suitable to process, store and/or communicate data during use. In another embodiment, the computer 112 and the Compton scattering inspection device 110 are provided in the form of a single device.

Figure 2:
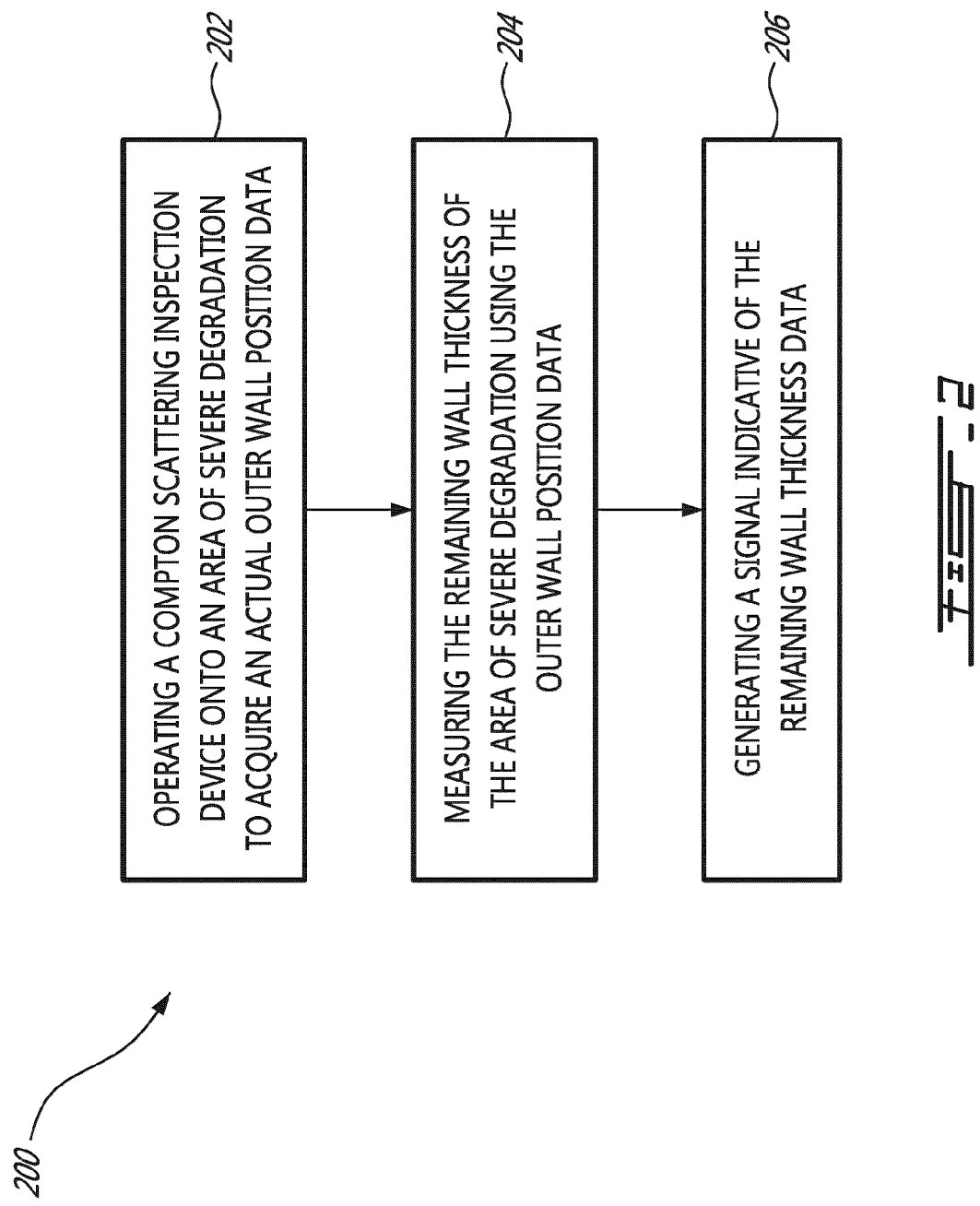
FIG. 2 is a flow chart of an example of a method for measuring a remaining wall thickness, in accordance with an embodiment.

Referring now to FIG. 2, the Compton scattering inspection device 110 and the computer 112 can be used to measure the remaining wall thickness 108 of the area of severe degradation 106 in accordance with the method shown at 200. More specifically, the method 200 has a step 202 of operating the Compton scattering inspection device 110 onto the area of severe degradation 106, across the composite wrap repair 104, in a manner to acquire an actual outer wall position data 114, which is best seen in FIG. 1B. The method 200 has a step of measuring, by using the computer 112, the remaining wall thickness 108 of the area of severe degradation 106 using at least the outer wall position data 114. The method 200 then has a step of generating, by using the computer 112, a signal indicative of the remaining wall thickness 108. Once measured, the remaining wall thickness 108 can be used to determine the integrity of the composite structure 100 as a whole, and especially the integrity of the area of severe degradation 106. In envisaged embodiment, the composite wrap repair 104 can be used as long as the remaining wall thickness 108 is deemed to be safe, thus prolonging the use of the composite wrap repair 104. Performing maintenance of the composite structure 100 can thus be more efficient and less costly.

Depending on the circumstances, the Compton scattering inspection device 110 can be operable to acquire an actual inner wall position data 116. In the embodiment shown in FIGS. 1A-B, the remaining wall thickness 108 is measured by performing a difference between the actual inner wall position data 116 and the actual outer wall position data 114. For instance, if the actual inner and outer wall position data 116 and 114 are distances from the Compton scattering inspection device 110, the remaining wall thickness 108 corresponds to the actual inner wall position data 116 minus the actual outer wall position data 114.

For some composite structures, as illustrated in FIG. 3, the Compton scattering inspection device 110 may not be able to acquire the actual inner wall position data, allowing only to acquire the actual outer position data 114. This can occur when the wall is too thick. In this case, the remaining wall thickness 108 can be measured using a nominal wall thickness 118 of the metal pipe 102. In an embodiment, the nominal wall thickness 118 is known a priori from a construction specification of the metal pipe 102 and used directly in the calculations. In another embodiment, the nominal wall thickness 118 is measured using either the Compton scattering inspection device 110 or an NDT device 400. An example of the NDT device 400 is an ultrasonic testing (UT) device. Such UT device provides satisfactory measurements when used on bare and/or clean metal surfaces. Measurements of the nominal wall thickness 118 at different positions along the metal pipe 102 can be averaged. Methods of measuring the nominal wall thickness 118 can vary. Alternatively, the nominal wall thickness 118 can also be measured by the difference of the actual outer wall position data 114 and the actual inner wall position data as measured with the Compton scattering inspection device 110 when the thickness of the wall of the metal pipe 102 allows such measurements.

In the embodiment shown in FIG. 3, measuring the remaining wall thickness 108 is performed by operating the Compton scattering inspection device 110 at a known distance 120 relative to a virtual unaltered outer wall position data 112, represented by the dashed line. It will be understood that the unaltered outer wall position data 112 corresponds to the actual outer wall position data 114 when the Compton scattering inspection device 110 is operated towards an unaltered area 126 of the metal pipe 102 from the known distance 120. In this embodiment, the Compton scattering inspection device 110 is maintained at the known distance 120, for instance at position P, using support such as a jig. Other ways of maintaining the Compton scattering inspection device 110 can also be used. By having the known distance 120, a pit depth 124 is measured using the computer 112 by performing a difference of the actual outer wall position 114 and the virtual unaltered outer wall position 122. Then, measuring the remaining wall thickness 108 is possible by subtracting the pit depth 124 from the nominal wall thickness 118. In another embodiment, measuring the remaining wall thickness 108 is performed by the computer 112 using a BCT image of the metal pipe 102. The BCT image typically results from the operation of the Compton scattering inspection device 110 along a linear section of the metal pipe 102 which includes successively an unaltered area 126, an area of severe degradation 106 and another unaltered area 126. For instance, in the case of the area of severe degradation 106 shown in FIG. 3, operating the Compton scattering device 110 along the linear section which is delimited by opposite edges of the composite wrap repair 104 is sufficient. Once the BCT image of the linear section is obtained, the computer 112 can draw a digital line in the BCT image which starts from the unaltered outer wall of the unaltered area 126 and ends to the unaltered outer wall of the other unaltered area 126, across the area of severe degradation 106. The measurement of the pit depth 124 can then be performed by measuring the distance between a depth associated with a deepest flawed region and the digital line, perpendicularly therefrom. The linear displacement path of the Compton scattering device does not need to be perfectly parallel to the length of the metal pipe 102. For instance, publication WO 2014/124,522 discloses a Compton scattering device which has means to be displaced linearly along a frame which can be positioned immobile relative to the metal pipe 102. Even if the frame slightly slopes relative to the metal pipe 102, the displacement path is linear and the measurement can be made.

It was found that this BCT apparatus has the possibility of penetrating across the composite wrap and obtaining precise information about the wall position underneath it. It was found that using such a BCT apparatus in combination with information about the wall thickness outside the composite repair can provide a satisfactorily precise indication of remaining wall thickness to assess the fitness of the asset for service. However, the BCT apparatus, at least in its current state of development, has a limited range, and operating it over the entire surface of the composite wrap repair is not considered interesting given the expected amount of time to perform such operation.

It was found, however, that simply determining an area in the composite wrap repair where the degradation is most severe, as opposed to precisely measuring a remaining wall thickness, can be suitably performed by another available NDT technique, such as Radiography, Digital Radiography, Pulsed Eddy Current (e.g. Incotest), etc.

Accordingly, by combining both techniques, the measuring of the remaining wall thickness can be specifically performed by the BCT apparatus at the location of most severe degradation determined using the other technique, which can provide for a satisfactory method overall.

Moreover, it was found that in many cases, composite wrap failure mechanisms such as dis-bonding between sheets or from the asset, could be satisfactorily evidenced by visual inspection. If areas are suspected, a bond tester (e.g. an Bond Tester such as manufactured by Elcometer) can be used to measure adhesion between layers of wrap. A Magnetic Lift Off Gauge can be used to measure total wrap thickness. Over time this measurement can be compared to a baseline to determine disbonding of layers of wrap, such as would be implied by increased thickness readings over time. This step can be performed by a Certified Weld Inspector (WCB) following a standardized visual assessment process.

A certified weld inspector because can be familiar with the assets and with typical visual inspection procedures in other contexts and would be able to rely on training and experience to make a judgement. Moreover, a visual inspection step can be a useful part of a condition assessment procedure as it could catch flaws that would go undetected by the steps of determining an area of most severe degradation and measuring a thickness of the wall at that area.

If a sum of all composite wrap repairs are considered for a large asset (e.g. offshore platform), the results of the visual inspection procedure could be combined with a form of ranking system in order to prioritize the set of repairs for more thorough inspection.

Example of Non-Destructive Inspection of a Repaired Section of Piping

Following visual inspection, an example method of determining an area of most severe degradation from corrosion on the outer surface of a metal pipe covered by a given composite wrap repair, and of measuring the remaining wall thickness at that area of most severe degradation is as follows:

Using ultrasonic testing, areas outside the wrap repair are tested to determine an average wall thickness value for the nominal wall of the pipe or vessel.

DWSI (Double Wall Single Image) radiography is performed on 360 degrees by a certified technician to provide a full view of the portion of the pipe or vessel covered by the composite wrap repair. The position of the area(s) of most severe degradation is determined using this full view.

Radiographing through both walls can lead to features on the wall nearest the source during scanning being projected onto the film from further away, causing the features to appear larger than they are, being imprecise. It may be required (via a technician or associated software) to differentiate between features seen on near wall vs. those seen on far wall and deduce from the radiographs not only the most severe defects but also a position with a satisfactory degree of accuracy. This can be performed as follows: i) positioning three identification markers 120 degrees apart on the outer diameter of the wrap (potentially adjust top and bottom of the image to ensure alignment); ii) taking a radiograph of all 3 shots and expose the film; iii) locating most severely degraded region using contrast meter; tracing features onto clear plastic film; iv) positioning plastic film over asset using alignment markers; and v) drawing target scan lines on wrap corresponding to areas of most severe degradation.

BCT is then applied to the area(s) of most severe degradation identified previously using the DWSI, to accurately measure external pit depth associated to the severity of the corrosion-imparted degradation on the external surface of the metal pipe. Assuming the integrity of the structure outside the composite repair is unaltered, external pit depth is then subtracted from nominal wall thickness determined from the ultrasonic testing, to determine remaining wall thickness, and a decision can be taken as to the fitness of the structure.

As can be understood, the examples described above and illustrated are intended to be exemplary only. For instance, the composite repair can be applied non-removably to a pressure vessel or even a flat metal surface, and can be made of a wide variety of composite materials unremovably (i.e. difficult or otherwise unpractical to remove and motivating inspection without removal) adhered to a portion of a metal structure such as a metal pipe, vessel or structure where the target metal structure can continue degrading/eroding/corroding on its outer surface underneath the composite repair. For example, some large metal vessels might be patched with a fiberwrap, or it could be simply an unremovable insulative material or other unremovable compound. Alternately to computed tomography where a tomographic slice of Compton scattering data is taken, a properly targeted probe at a singular location can be satisfactory in some embodiments, as can be a set of evenly spaced probed measurements. Many forms of collection can be used and be considered Compton scattering data. The process of identifying the area of severe degradation can be automated more than described above, for instance, and the step of orienting the Compton scattering inspection device toward the location of most severe degradation can be performed manually or in an automated manner, for instance. Moreover, in an alternate embodiment, where the wall thickness is appropriate to allow the Compton scattering inspection device to penetrate entirely across the wall and reach the inner wall, the remaining wall thickness can be determined based on a pre-calibrated correlation between total count of the detected particles and remaining wall thickness. Accordingly, the scope is indicated by the appended claims.

What is claimed is:

1. A method of measuring a remaining wall thickness of a composite structure, the method comprising:
    performing an inspection of the composite structure having a plurality of portions;
    identifying one of the portions having an area of severe degradation based on the results of the inspection performed;
    operating a Compton scattering inspection device onto the area of severe degradation, in a manner to acquire at least an actual outer wall position data;
    using a computer, measuring the remaining wall thickness of the area of severe degradation using at least the outer wall position data;
    generating a signal indicative of said remaining wall thickness; and
    obtaining a nominal wall thickness of the one of the portions having an area of severe degradation in an unaltered state;
    wherein the step of operating the Compton scattering inspection device is performed at a known distance from a virtual unaltered outer wall position and includes measuring a pit depth based on the difference between the actual outer wall position and the virtual unaltered outer wall position; and said measuring includes subtracting the pit depth from the nominal wall thickness.

2. The method of claim 1 wherein the step of operating the Compton scattering inspection device is performed in a manner to further acquire an actual inner wall position data, and the step of measuring includes performing a difference between the actual inner wall position data and the actual outer wall position data.

3. The method of claim 1 wherein said obtaining the nominal wall thickness includes acquiring the nominal wall thickness from a specification of the composite structure.

4. The method of claim 1 wherein the composite structure is a metal surface covered by a composite repair at the area of severe degradation.

5. The method of claim 1 further comprising performing maintenance of the composite structure based on the signal indicative of said remaining wall thickness.

6. The method of claim 1 wherein said performing the inspection is performed using a nondestructive testing device.

7. The method of claim 1 wherein the composite structure is a metal surface covered by a composite repair at the area of severe degradation.

* * * * *